US005462965A

United States Patent [19]
Roba et al.

[11] Patent Number: 5,462,965
[45] Date of Patent: Oct. 31, 1995

[54] USE OF HETEROCYCLIC AMINO-ALCOHOL COMPOUNDS FOR TREATMENT OF CNS DISEASES

[75] Inventors: Joseph L. Roba, Dion-Valmont; Claude L. Gillet, Blanmont, both of Belgium; Michael F. Rafferty, Buffalo Grove, Ill.; Bevyn Jarrott, Diamond Creek; Philip M. Beart, Ivanhoe, both of Australia

[73] Assignee: GD Searle & Co., Skokie, Ill.

[21] Appl. No.: 949,815

[22] PCT Filed: Jul. 22, 1991

[86] PCT No.: PCT/US91/05028

§ 371 Date: Dec. 7, 1992

§ 102(e) Date: Dec. 7, 1992

Related U.S. Application Data

[63] Continuation-in-part of Ser. No. 566,744, Aug. 13, 1990, abandoned.

[51] Int. Cl.$^6$ .................. A61K 31/38; A61K 31/535; A61K 31/495; A61K 31/445; A61K 31/415; A61K 31/40; A61K 31/35; A61K 31/34; A61K 31/135

[52] U.S. Cl. .................. 514/443; 514/233.5; 514/238.8; 514/253; 514/317; 514/324; 514/392; 514/422; 514/431; 514/432; 514/416; 514/456; 514/469; 514/653; 514/649; 514/650

[58] Field of Search .................. 514/649, 650, 514/653, 233.5, 238.8, 253, 317, 324, 392, 422, 431, 432, 416, 443, 456, 469, 649, 650, 653

[56] References Cited

U.S. PATENT DOCUMENTS

| | | | |
|---|---|---|---|
| 4,638,070 | 1/1987 | Lambelin et al. | 549/9 |
| 4,657,899 | 4/1987 | Rzeszotarski | 514/120 |
| 4,791,104 | 12/1988 | Picciola et al. | 514/58 |
| 4,826,975 | 5/1989 | Picciola et al. | 544/391 |
| 4,882,352 | 11/1989 | Horn | 514/438 |
| 4,902,799 | 2/1990 | Picciola et al. | 546/199 |
| 5,071,858 | 12/1991 | Hutchison | 514/324 |

FOREIGN PATENT DOCUMENTS 0362941 4/1990 European Pat. Off. .

OTHER PUBLICATIONS

S. M. Rothman et al, *Annals of Neurology*, vol. 19, No. 2, 105–f111 (1986).
K. Matoba et al, "Structural Modification of Bioactive Compounds II. Syntheses of Aminophosphonoic Acids", Chem. Pharm. Bull., 32, 3918–2925 (1984).

C. Carter et al, *J. Pharm. Exp. Ther.*, 247, 1222–1232 (1988).

P. M. Beart et al, *Neurosci, Lett.*, 124, 187–189 (1991).

P. C. Contreras et al, *Neurosci. Lett.*, 116, 190–193 (1990).

J. Benavides et al, *Neurosci. Abstracts*, 16, 541 (1990).

A. F. Gilman et al, *The Pharmacological Basis of Therapeutics*, 7th Edn., p. 404, MacMillan (1985).

M. N. Perkins et al, *Neuroscience Lett.*, 23, 333 (1981).

J. Davies et al, *Neuroscience Lett.*, 21, 77–81 (1981).

D. E. Murphy et al, *J. Pharmacol, Exp. Ther.*, 240 (3), 778–784 (1987).

Z. J. Vejdelek et al, Collection Czechoslov. Chem. Commun., 39(2), 617–623 (1974).

J. Q. Qian et al, *Arch. Int. Pharmacodyn*, 266 (2), 264–281 (1983).

J. Lehmann, *Drug News Perspect.*, 4 (1), 57–61 (1991).

J. A. Kema et al, *Trends in Neurosciences*, 10, (7) 294–298 (1987).

Primary Examiner—Theodore J. Criares
Attorney, Agent, or Firm—Joseph W. Bulock; J. Timothy Keane

[57] ABSTRACT

A class of heterocyclic amino-alcohol compounds is described for treatment of CNS-related diseases, namely, for use as a neuroprotective agent, to reduce neurotoxic injury associated with conditions of hypoxia, anoxia or ischemia which typically follows stroke, myocardial infarct, perinatal asphyxia, or hypoglycemic events. Other examples of treatable CNS-related diseases include neurodegenerative diseases such as Parkinson's disease, Huntington's chorea and Alzheimer's disease, and also psychotic disorders such as schizophrenia. The treatment includes administration of a compound of this class alone or in a composition in an amount effective as a mediator to alter excitatory actions at the NMDA excitatory amino acid receptor complex. A compound of this class of specific interest is the following:

9 Claims, No Drawings

USE OF HETEROCYCLIC AMINO-ALCOHOL COMPOUNDS FOR TREATMENT OF CNS DISEASES

RELATED APPLICATIONS

This is a continuation-in-part of U.S. application Ser. No. 07/566,744 filed on Aug. 13, 1990, now abandoned. This application is a continuation of PCT\US91\05028, filed Jul. 22, 1991.

FIELD OF INVENTION

This invention is in the field of clinical neurology and relates specifically to a class of compounds, compositions and methods for CNS-disease treatment, such as for controlling or treating chronic or acute neuronoxic injury or brain damage resulting from ischemic conditions, and for treating certain neurodegnerative diseases.

These compounds would be particularly useful for treating neurotoxic injury which follows periods of hypoxia, anoxia, or ischemia associated with stroke, cardiac arrest, perinatal asphyxia or hypoglycemic events.

BACKGROUND OF THE INVENTION

Unlike other tissues which can survive extended periods of hypaxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by the specific antagonism of postsynaptic glutamate receptors [see S. M. Rothman et al, *Annals of Neurology*, 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS). Glutamate is believed to be a mixed agonist capable of binding to and exciting all three receptor types.

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with anoxia, hypoxia or ischemia caused by stroke, cardiac arrest or perinatal asphyxia.

It is known that compounds of various structures, such aminophosphonovalerate derivatives and piperidine dicarboxylate derivatives, may act as competitive antagonists at the NMDA receptor. In particular, compounds such as 2-amino-4-(2-phosphonomethylphenyl)butyric acid and 2-(2-amino-2-carboxy)ethylphenylphosphonic acid have been synthesized for evaluation as antagonists in blocking the action of the neurotransmitter compounds L-glutamic acid and L-aspartic acid [K. Matoba et al, *Chem. Pharm. Bull.*, 32 (10), 3918–3925 (1984)].

There is other evidence that the NMDA receptor complex is involved in multiple physiological and pathological events, inasmuch as the NMDA receptor complex is a ligandgated ion channel that can be modulated by diverse substances acting at distinct recognition sites. For example, there is evidence that polyamines including spermine and spermidine profoundly enhance the binding of channel ligands, such as [$^3$H]TCP(N-1-[2-thienyl]cyclohexyl)piperidine) and [$^3$H]dizocilipine (MK-801) by acting as agonist modulators, like glycine. Polyamines may act by increasing the frequency of channel opening or by increasing the duration of the open state.

Certain piperidineethanol derivatives, such as ifenprodil and 1-(4chlorophenyl)-2-[1-(4-fluorophenyl)piperidinyl]ethanol, which are known anti-ischemic agents, have been found to be noncompetitive NMDA receptor antagonists [C. Carter et al, *J. Pharm Exp. Ther.*, 247 (3), 1222–1232 (1988)]. Also, tritiated and iodinated ifenprodil molecules have been employed to examine the characteristics of the polyamine domain of the NMDA receptor-complex [P. M. Beart et al, *Neurosci. Lett.*, 124, 187–189 (1991)].

It has been found that ifenprodil has considerable affinity for the sigma site in vitro [P. C. Contreras et al, *Neurosci. Lett.*, 116, 190–193 (1990)]. Sigma binding affinity has also been found in vivo and it has been further suggested that sigma ligands may have neuroprotective properties [J. Benavides et al, *Neurosci. Abstracts*, 16, 541 (1990)].

There are many classes of compounds known for treatment of psychotic disorders. For example, current therapeutic treatments for psychoses use compounds classifiable as phenohiazine-thioxanthenes, as phenylbutylpiperidines and also as certain alkaloids. An example of a phenylbutylpiperidine compound of current use in psychotic treatment therapy is haloperidol [A. F. Gilman et al, *The Pharmcological Basis of Therapeutics*, 7th Edn., p. 404, MacMillan (1985)].

The reference 'Collection Czechoslov. Chem. Comun.', 39 (2), 617–623, 1974, describes some phenylaminoethanols which in certain cases and mostly high doses posess a CNS-activity. These are 1-(5-indanyl)-2-amino-N,N-n-butyl-methylethanol, 1-(5-indanyl)-2-amino-N-phenylmethylpiperazinoethanol and 1-(5-indanyl)-2-amino-N-cycloheptyl-ethanol.

The reference Arch. Int. Pharm., 266 (2), 264–281, 1983 discloses the antihypertensive effect of Tibalosine—a t ienylphenyl-aminoethanol—which is said to also exhibit anxiolytic activity. The reference, however, is silent with respect to a NMDA-antagonisic and neuro-protective effect of said compound.

DESCRIPTION OF THE INVENTION

A neuroprotective effect is provided in a subject by treating a subject susceptible to, or afflicted with, neurotoxic injury or a neurodegenerative disease with a therapeutically-effective amount of a compound characterized in having activity as a mediator or as an inhibitor at a major neuronal excitatory amino acid receptor site, such as the NMDA receptor site. Such receptor mediator or inhibitor compounds may be selected from a class of heterocyclic aminoalcohol compounds defined by Formula I:

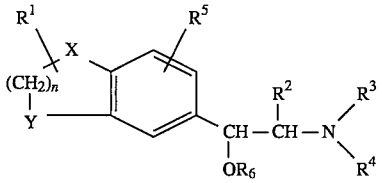

wherein X is selected from oxygen atom, sulfur atom, —$CH_2$— and —NH—;

wherein Y is selected from —$CH_2$— and —NH—;

wherein n is a number selected from one through three, inclusive;

wherein $R^1$ is selected from hydrido, alkyl, hydroxyalkyl, alkoxyalkyl, cycloalkyl, cycloalkylalkyl, phenyl and carboxyl;

wherein $R^2$ is selected from hydrido, alkyl, hydroxyalkyl, cycloalkyl and cycloalkylalkyl;

wherein each of $R^3$ and $R^4$ is independently selected from hydrido, alkyl, haloalkyl, cycloalkyl, cycloalkylalkyl, alkylcycloalkyl, alkylcycloalkylalkyl, phenyl, phenylalkyl, diphenylalkyl, alkylphenyl, alkylphenylalkyl, halophenyl, halophenylalkyl, phenoxyalkyl, halophenoxyalkyl, alkoxyphenoxyalkyl, cyanophenoxyalkyl, benzyloxyalkyl, alkoxyalkyl, alkoxyalkoxyalkyl, alkoxycarbonylalkyl, phenylthioalkyl, alkylcarbonylaminophenylalkyl, halophenylcarbonylalkyl, halobenzylcarbonylalkyl, alkylcarbonylphenoxyalkyl, alkoxycarbonylphenoxyalkyl, alkylphenoxyalkyl, alkenylalkyl, alkynylalkyl, alkynylalkyloxyalkyl, polycycloalkyl, saturated or partially unsaturated heterocyclic, saturated or partially unsaturated heterocyclicalkyl, heteroarylalkyl and heteroaryloxyalkyl;

wherein $R^3$ and $R^4$ may be taken together to form a saturated or partially unsaturated heterocyclic group or a heteroaryl group, either of which groups may be further substituted, said groups selected from alkylphenylpiperidinyl, morpholino, phenylmorpholino, alkylmorpholino, 1-alkyl-2-phenylmorpholino, phenylalkylpiperidinyl, phenylpiperidinyl, phenylalkylpyrrolidinyl and phenylalkylpiperazinyl;

wherein $R^5$ is selected from hydrido, alkyl, hydroxyalkyl, cycloalkyl, cycloalkylalkyl, phenylalkyl and phenyl;

wherein $R^6$ isSelected from hydrido, alkanoyl and cycloalkanoyl;

and wherein any of the foregoing $R^1$–$R^6$ radicals may be further substituted at a substitutable position with a radical selected from alkyl, cycloalkyl, cycloalkylalkyl, alkoxy, alkenylalkyl, alkoxyalkyl, hydroxyalkyl, oxo, cyano, halo, phenyl and phenylalkyl;

or a pharmaceuticallyacceptable salt thereof.

The invention does not comprise the use of compounds of Formula I wherein X, Y are $CH_2$, n=1, $R^1$, $R^2$, $R^5$, $R^6$ are H and $R^3$ is n-butyl, $R^4$ methyl or $R^3$, $R^4$ are phenylmethylpiperazinyl or $R^3$, $R^4$ are N-cycloheptyl.

A preferred class of compounds consists of compounds of Formula I wherein X is selected from oxygen atom, sulfur atom, —$CH_2$— and —NH—;

wherein Y is selected from —$CH_2$— and —NH—;

wherein n is a number selected from one through three, inclusive;

wherein $R^1$ is selected from hydrido, alkyl, hydroxyalkyl, cycloalkyl, phenyl and carboxyl;

wherein $R^2$ is selected from hydrido, alkyl and cycloalkyl;

wherein each of $R^3$ and $R^4$ is independently selected from hydrido, methyl, ethyl, n-propyl, isopropyl, n-butyl, isobutyl, sec-butyl, iso-butyl, tert-butyl, n-pentyl, neopentyl, iso-pentyl, n-hexyl, n-heptyl, n-octyl, n-nonyl, n-decyl, n-undecyl, n-duodecyl, n-tredecyl, n-tetradecyl, cyclopropyl, cyclobutyl, cyclopentyl, cyclohexyl, cycloheptyl, cyclohexyl, cyclooctyl, cyclononyl, cyclohexylmethyl, cyclohexylethyl, cyclohexylpropyl, cyclohexylbutyl, methylcyclohexylbutyl, phenyl, benzyl, phenylethyl, phenylpropyl, phenylbutyl, phenylpentyl, phenylhexyl, diphenylmethylethyl, diphenylmethylpropyl, methylphenyl, methylphenylmethyl, methyphenylethyl, methylphenylpropyl, methylphenylbutyl, chlorophenylbutyl, fluorophenylbutyl, phenoxyethyl, phenoxypropyl, phenoxybutyl, dimethoxyphenylethyl, chlorophenoxyethyl, dichlorophenoxyethyl, methylphenoxyethyl, methoxyphenoxyethyl, dimethoxyphenoxyethyl, cyanophenoxyethyl, benzyloxyethyl, butoxypropyl, butoxyethoxypropyl, methoxycarbonyldecyl, methoxyethoxypropyl, butoxypropoxypropyl, phenylthioethyl, phenylthiopropyl, phenylthiobutyl, methylcarbonylaminophenoxyethyl, fluorophenylcarbonylpropyl, fluorobenzylcarbonylpropyl, ethylcarbonylphenoxyethyl, methoxycarbonylphenoxyethyl, tert-butylphenoxyethyl, alkenylalkyl, propargylpropyl, propargylbutyl, propargylpentyl, propargylhexyl, propargylpropyloxypropyl, methylsulfonylaminophenoxybutyl, adamantyl, imidazolidonepropyl, pyrrolidinylmethyl, pyrrolidinenylethyl, pyrrolidinylpropyl, naphthyloxyethyl, naphthyloxypropyl, indanoyloxyethyl, indanoyloxypropyl, pyrrolidinylmethyl and pyrrolidinylethyl;

wherein $R^3$ and $R^4$ may be taken together to form a saturated or partially unsaturated heterocyclic group or a heteroaryl group, either of which groups may be further substituted, said groups selected from methylphenylpiperidinyl, morpholino, phenylmorpholino, methylmorpholino, 1-methyl-2-phenylmorpholino, phenylmethylpiperidinyl, phenylpiperidinyl, phenylmethylpyrrolidinyl and phenylmethylpiperazinyl;

wherein $R^5$ is selected from hydrido, alkyl and cycloalkyl;

wherein $R^6$ is selected from hydrido, alkanoyl and cycloalkanoyl;

and wherein any of the foregoing $R^1$–$R^6$ radicals may be further substituted at a substitutable position with a radical selected from alkyl, cycloalkyl, alkenylalkyl, alkoxyalkyl, hydroxyalkyl, oxo, cyano, halo, phenyl and phenylalkyl;

or a pharmaceuticallyacceptable salt thereof.

A more preferred class of compounds consists of compounds of Formula I wherein $R^1$ is selected from hydrido, linear or branched $C_1$ to $C_3$ alkyl radicals, a phenyl radical and a carboxyl radical;

wherein $R^2$ is selected from a linear or branched $C_1$ to $C_3$ alkyl radical;

wherein $R^3$ is selected from a mono or polyunsaturated $C_3$ to $C_{18}$ alkenyl radical; a mono or polyunsaturated $C_3$ to $C_{12}$ alkenyl radical substituted by phenyl and optionally containing an oxygen or sulfur linkage; a mono or polyunsaturated $C_3$ to $C_{18}$ alkynyl radical; a mono or polyunsaturated $C_3$ to $C_{12}$ alkynyl radical substituted by phenyl and optionally containing an oxygen or sulfur linkage; a cycloalkyl $C_3$ to $C_{10}$ radical; a $C_2$ to $C_{20}$ linear or branched alkyl radical; a linear or branched $C_2$ to $C_{18}$ alkyl radical, containing at least one oxygen or sulfur linkage and optionally substituted with one or more groups selected from $C_1$ to $C_3$ alkoxycarbonyl, pyrrolidine, pyrrolidinone, imidazolidone, phenyl, phenoxy, phenylthio, benzoyl, indanyloxy, naphthyloxy, and phenyl, phenoxy, phenylthio and benzoyl radicals substituted by one or more $C_1$ to $C_4$ alkyl or $C_1$ to $C_4$ alkoxy radicals, by one or two halogen atoms, or by a nitrile, hydroxy, amino, $C_2$ to $C_6$ alkylcarbonyl, $C_2$ to $C_4$ acylamino, $C_2$ to $C_5$ alkoxycarbonyl, or $C_1$ to $C_4$ alkylsulfonamido radical, or by an alkoxycarbonylalkyl in which both the alkoxy and alkyl moieties contain from 1 to 4 carbon atoms, or alkoxycarbonylalkoxy in which each alkoxy moiety contains from 1 to 4 carbon atoms;

wherein $R^4$ is hydrido or when taken with $R^3$ and adjacent nitrogen atom, forms a morpholine, pyrrolidine, piperidine radical or a piperidine radical substituted by one or two $C_1$ to $C_4$ alkyl, phenyl or phenylalkyl ($C_1$ to $C_4$) radicals, or a piperazine radical substituted in position 4 by a phenyl radical or by a phenyl radical itself substituted by one or ($C_1$ to $C_4$) two alkyl or ($C_1$ to $C_4$) alkoxy radicals, one or two halogen atoms, or a trifluoromethyl radical;

wherein $R^5$ is selected from hydrido, halogen, and a $C_1$ to $C_3$ alkyl radical;

wherein $R^6$ is selected from a hydrido, a linear or branched $C_2$ to $C_{11}$ alkylcarbonyl radical and a $C_3$ to $C_8$ cycloalkyl carbonyl radical;

wherein n is selected from one, two and three;

wherein X is selected from sulfur, oxygen, a —$CH_2$— radical or a —NH— radical;

wherein Y is selected from a —$CH_2$— radical or sulfur provided that when simultaneously X is oxygen, Y is —$CH_2$— group, n is 2, each of $R^1$ and $R^5$ is hydrido, $R^2$ is methyl and $R^8$ is hydrido or an alkyl carbonyl radical, $R^4$ does not form a substituted piperazine radical with $R^3$ and the adjacent nitrogen atom; or a pharmaceuticallyacceptable salt thereof.

An even more preferred family of compounds consists of compounds of Formula I wherein $R^1$ is hydrido or alkyl ($C_1$ to $C_3$) radical;

wherein $R^2$ is selected from alkyl ($C_1$ to $C_3$) radical;

wherein $R^3$ is selected from a mono or polyunsaturated alkenyl ($C_3$ to $C_{18}$) radical; a mono or polyunsaturated alkynyl ($C_3$ to $C_{18}$) radical; a cycloalkyl ($C_3$ to $C_8$) radical; an alkyl ($C_2$ to $C_{18}$) radical; an alkyl ($C_2$ to $C_{18}$) radical substituted by a group selected from phenylthio radical, an alkoxy ($C_1$ to $C_6$) radical, an alkythio ($C_1$ to $C_6$) radical, a phenoxy radical, a benzoyl radical and one or two phenyl radicals; a group selected from a phenyl, benzoyl, phenylthio or phenoxy radical each substituted by an alkyl ($C_1$ to $C_3$) or a halogen; a group selected from a phenoxy radical substituted by a nitrile or an alkylcarbonyl ($C_2$ to $C_3$) radical;

wherein $R^4$ is hydrido or when taken with $R^3$ and the adjacent nitrogen atom forms a group selected from a piperidine radical substituted by a phenyl radical which is in turn substituted by an alkyl ($C_1$ to $C_3$) radical and a group selected from a piperidine radical substituted by an alkyl ($C_1$ to $C_3$) radical which is itself substituted by a phenyl radical;

wherein $R^6$ is selected from hydrido and alkyl ($C_1$ to $C_3$) radical;

wherein $R^6$ is selected from hydrido, a linear or branched alkylcarbonyl ($C_2$ to $C_9$) radical and a cycloalkylcarbonyl ($C_3$ to $C_6$)radical;

wherein n is selected from a number selected from one, two and three;

wherein X is selected from sulfur atom, oxygen atom and —NH— radical;

wherein Y is selected from a —$CH_2$— radical and sulfur atom;

or a pharmaceutically-acceptable salt thereof.

A highly preferred family of compounds consists of compounds of Formula I wherein $R^1$ is selected from hydrido and one or two linear or branched $C_1$ to $C_3$ alkyl radicals; wherein $R^2$ is selected from alkyl ($C_1$ to $C_3$) radical;

wherein $R^3$ is selected from $C_3$ to $C_{18}$ alkenyl radical; $C_3$ to $C_{18}$ alkynyl radical; $C_3$ to $C_{18}$ cycloalkyl radical; linear or branched $C_2$ to $C_{18}$ alkyl radical; linear or branched $C_2$ to $C_{18}$ alkyl radical containing one or more oxygen or sulfur linkages, and optionally substituted by at least one or more groups selected from alkoxycarbonyl, pyrrolidine, pyrrolidinone or imidazolidone radical, by one or two phenyl, phenoxy, phenylthio, indanyloxy radicals; one or more groups selected from phenyl, phenoxy, phenylthio radical substituted by one or two $C_1$ to $C_4$ alkyl or $C_1$ to $C_4$ alkoxy radicals; or one or two halogen atoms; one or more groups selected from nitrile, hydroxy, amino, $C_2$ to $C_9$ alkyl carbonyl, $C_2$ to $C_4$ acylamino, alkoxycarbonyl, or $C_1$ to $C_4$ alkylsulfonamido radical, or one or more groups selected from alkoxycarbonylalkyl in which the alkyl and alkoxy moieties contain from 1 to 4 carbon atoms, or alkoxy carbonyl alkoxy in which each alkoxy moiety contains from 1 to 4 carbon atoms;

wherein X is selected from sulfur, oxygen and a —$CH_2$— radical; and Y is a —$CH_2$— radical.

A class of compounds of very high interest consists of compounds of Formula II

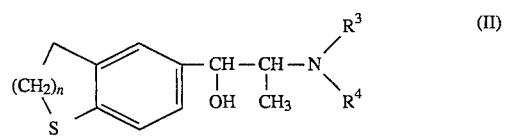

(II)

wherein n is one or two; wherein $R^4$ is hydrido; wherein $R^3$ is selected from phenylpropyl, phenylbutyl, phenylpentyl, phenoxypropyl, phenoxybutyl and phenylpentyl, wherein the propyl and butyl radicals may be linear or branched; and wherein $R^3$ and $R^4$ may be taken together to form phenylmethylpiperidinyl; or a pharmaceutically-acceptable salt thereof.

Specific compounds of interest within Formula I are compounds, and their pharmaceuticallyacceptable salts, of the following group:

1-(6-thiochromanyl)-2-n-octylamino-1-propanol;
1-(6-thiochromanyl)-2-(4-phenylbutylamino)-1-propanol;
1-(6-thiochromanyl)-2-[2-(phenoxy)ethylamino]-1-propanol;
1-(2,3-dihydro-5-benzo(b)thienyl)-2-n-octylamino-1-propanol;

1-(2,3-dihydro-5-benzo(b)thienyl-2-(4-phenylbutylamino)-1-propanol;
1-(2,3-dihydro-5-benzo(b)thienyl)-2-[4-(p-chlorophenyl)butylamino]-1-propanol;
1-(2-methyl-2,3-dihydro-5-benzo(b)thienyl)-2-(4-phenylbutylamino)-1-propanol;
1-(2-methyl-2,3-dihydro-5-benzo(b)furanyl)-2-n-octylamino-1-propanol;
1-(2,3,4,5-tetrahydrobenzo(b)thiepin-7-yl)-2-(4-phenylbutylamino)-1-propanol;
1-(2,3-dihydro-5-indolyl)-2-n-octylamino-1-propanol;
1-(2,3-dihydro-5-benzo(b)thienyl)-2-(4-phenylbutylamino)-1-propionyl-oxypropane;
1-(2,3-dihydro-5-benzo(b)thienyl)-2-(4-phenylbutylamino)-1-cyclohexyl-carbonyloxypropane;
1-(5-indanyl)-2-(4-phenylbutylamino)-1-propanol;
1-(5-indanyl)-2-[2-(4-chlorophenoxy)ethylamino]-1-propanol;
and 1-(5-indanyl)-2-[2-(4-fluorobenzoyl)propylamino]1-propanol.

Compounds of particular interest are shown in Table I. Compounds of most particular interest are Compound #7 (which is the erythro form of 1-(2,3-dihydro-5-benzo[b]thienyl)-2-(4-phenylbutylamino-1-propanol; also known as tibalosine), Compound #2, Compound #24, Compound #26, Compound #42, Compound #75, Compound #183 (which is the threo form of tibalosine), Compound #184 (which is the (−)-isomer of tibalosine), Compound #185 (which is the (+)-isomer of tibalosine) and Compound #186.

Compounds of Formula I may be prepared by methods shown in U.S. Pat. No. 4,638,070.

Representative compounds of Formula I are shown in Table I, wherein Compounds #1–#186 are defined with reference to Formula I

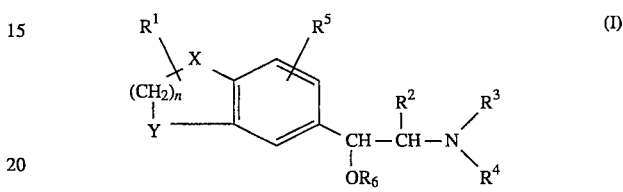

with substituents X, Y, n and $R^1$–$R^6$ defined in Table I, as follows:

TABLE I

| Cpd. # | X | Y | n | $R^1$ | $R^2$ | $R^3$ $-N\diagdown R^4$ | $R^5$ | $R^6$ | MP (°C.) [1][4] |
|---|---|---|---|---|---|---|---|---|---|
| 1 | S | $CH_2$ | 2 | H | $CH_3$ | —NHnC$_8$H$_{17}$ | H | H | 115–116 (acetone) |
| 2 | S | $CH_2$ | 2 | H | $CH_3$ | —NH—(CH$_2$)$_4$—C$_6$H$_5$ | H | H | 131–133 (acetone) |
| 3 | S | $CH_2$ | 1 | H | $CH_3$ | —NHnC$_8$H$_{17}$ | H | H | 118–120 (acetone) |
| 4 | S | $CH_2$ | 2 | 2-$CH_3$ | $CH_3$ | —NHnC$_8$H$_{17}$ | H | H | 116–117 ($CH_3OH$) |
| 5 | S | $CH_2$ | 2 | 2-$CH_3$ | $CH_3$ | —NH—(CH$_2$)$_4$—C$_6$H$_5$ | H | H | 118–119 ($CH_3OH$) |
| 6 | S | $CH_2$ | 1 | H | $CH_3$ | —NH—(CH$_2$)$_2$—C$_6$H$_5$ | H | H | 134–137 (acetone) |
| 7 | S | $CH_2$ | 1 | H | $CH_3$ | —NH—(CH$_2$)$_4$—C$_6$H$_5$ | H | H | 113–115 (acetone) |
| 8 | S | $CH_2$ | 2 | H | $CH_3$ | —NH—(CH$_2$)$_5$—C$_6$H$_5$ | H | H | 119–120 ($CH_3OH$) |
| 9 | S | $CH_2$ | 2 | 2-$CH_3$ | $CH_3$ | —NH—(CH$_2$)$_2$—C$_6$H$_5$ | H | H | 125–126 ($CH_3OH$) |
| 10 | S | $CH_2$ | 2 | 2-$CH_3$ | $CH_3$ | —N(piperazinyl)—C$_6$H$_4$(CH$_3$) | H | H | 149–151 (acetone) |

TABLE I-continued

| Cpd. # | X | Y | n | R¹ | R² | -N(R³)(R⁴) | R⁵ | R⁶ | MP (°C.) [1][4] |
|---|---|---|---|---|---|---|---|---|---|
| 11 | S | CH₂ | 3 | H | CH₃ | —NH—nC₈H₁₇ | H | H | 221–223 (CH₃OH-Et₂O)[2] |
| 12 | S | CH₂ | 3 | H | CH₃ | —NH—(CH₂)₄—C₆H₅ | H | H | 87–69 (acetone) |
| 13 | S | CH₂ | 2 | H | CH₃ | —NH—(CH₂)₂—C₆H₅ | H | H | 118–120 (acetone) |
| 14 | S | CH₂ | 3 | H | CH₃ | —NH—(CH₂)₂—C₆H₅ | H | H | 115–117 (acetone) |
| 15 | S | CH₂ | 2 | H | CH₃ | —N(piperazinyl)-2-CH₃-C₆H₄ | H | H | 165–166 (acetone) |
| 16 | S | CH₂ | 2 | H | CH₃ | —NH(CH₂)₂—CH(C₆H₅)₂ | H | H | 119–120 (acetone) |
| 17 | S | CH₂ | 2 | H | CH₃ | —NH—(CH₂)₃—C₆H₅ | H | H | 110–111 (acetone) |
| 18 | S | CH₂ | 1 | 2-CH₃ | CH₃ | —NH—nC₈H₁₇ | H | H | 70–72 (acetone) |
| 19 | S | CH₂ | T | 2-CH₃ | CH₃ | —NH—(CH₂)₄—C₆H₅ | H | H | 89–90 (MeOH) |
| 20 | S | CH₂ | 2 | H | CH₃ | —NH—CH₂CH₂O—C₆H₅ | H | H | 117–118 (acetone) |
| 21 | S | CH₂ | 2 | H | CH₃ | —NHCH₂CH(C₆H₅)₂ | H | H | 119–121 (CH₃OH) |
| 22 | S | CH₂ | 2 | H | CH₃ | —NHCH₂CH₂—C₆H₃(OCH₃)₂ | H | H | 131–133 (acetone) |

TABLE I-continued

| Cpd. # | X | Y | n | R¹ | R² | $-N\begin{smallmatrix}R^3\\R^4\end{smallmatrix}$ | R⁵ | R⁶ | MP (°C.) [1][4] |
|---|---|---|---|---|---|---|---|---|---|
| 23 | S | CH₂ | 2 | H | CH₃ | —NH—(CH₂)₄—C₆H₄—Cl | H | H | 106–107 (acetone) |
| 24 | S | CH₂ | 2 | H | CH₃ | —NH—(CH₂)₄—O—C₆H₅ | H | H | 141–144 (AcOEt) |
| 25 | S | CH₂ | 2 | H | CH₃ | —NH—(CH₂)₄S—C₆H₅ | H | H | 141–142 (CHCl₃) |
| 26 | S | CH₂ | 2 | H | CH₃ | —N(piperidin-4-yl)—CH₂—C₆H₅ | H | H | 126–127 (acetone) |
| 27 | S | CH₂ | 2 | H | CH₃ | —NHcycloC₈H₁₅ | H | H | 88–89 (C₆H₆ Petroleum ether) |
| 28 | S | CH₂ | 1 | H | CH₃ | —NHcycloC₈H₁₅ | H | H | 97–99 (acetone) |
| 29 | S | CH₂ | 1 | H | CH₃ | —NH—(CH₂)₄—C₆H₄—Cl | H | H | 120–122 (acetone) |
| 30 | S | CH₂ | 3 | H | CH₃ | —NH—(CH₂)₄—C₆H₄—CH₃ | H | H | 90–92 (acetone) |
| 31 | S | CH₂ | 1 | H | CH₃ | —NH—(CH₂)₄—S—C₆H₅ | H | H | 146–148 (MeOH—CHCl₃) |
| 32 | S | CH₂ | 1 | H | CH₃ | —NH—(CH₂)₄—C₆H₁₀—CH₃ | H | H | 128–130 (MeOH) |
| 33 | S | CH₂ | 1 | H | CH₃ | —NHiscC₃H₇ | H | H | 127–129 (acetone) |
| 34 | S | CH₂ | 2 | H | CH₃ | —NH—(CH₂)₄—C₆H₁₀—CH₃ | H | H | 126–127 (MeOH—CHCl₃) |
| 35 | S | CH₂ | 1 | H | CH₃ | —NH—(CH₂)₄—C₆H₅ | H | H | 131–133 acetone) |
| 36 | S | CH₂ | 3 | H | CH₃ | —NH—(CH₂)₂—O—C₆H₅ | H | H | 90–92 (MeOH) |
| 37 | S | CH₂ | 2 | H | CH₃ | —NH—(CH₂)₃—S—C₆H₅ | H | H | 95–96 (acetone) |
| 38 | S | CH₂ | 3 | H | CH₃ | —NHiscC₃H₇ | H | H | 107–109 (acetone) |

TABLE I-continued

| Cpd. # | X | Y | n | R¹ | R² | −N(R³)(R⁴) | R⁵ | R⁶ | MP (°C.) [1][4] |
|---|---|---|---|---|---|---|---|---|---|
| 39 | S | $CH_2$ | 3 | H | $CH_3$ | $-NH-(CH_2)_3-S-C_6H_5$ | H | H | 102–104 (acetone) |
| 40 | S | $CH_2$ | 2 | H | $CH_3$ | $-NH-(CH_2)_2-O-C_6H_4-Cl$ | H | H | 123–124 (acetone) |
| 41 | S | $CH_2$ | 2 | H | $CH_3$ | −NH−cyclohexyl | H | H | 97–98 (hexane-$Et_2O$) |
| 42 | S | $CH_2$ | 2 | H | $CH_3$ | $-NHCH(CH_3)-(CH_2)_3-C_6H_5$ | H | H | 94–95 ($Et_2O$) |
| 43 | S | $CH_2$ | 2 | 3-$CH_3$ | $CH_3$ | $-NHnC_8H_{17}$ | H | H | 70–72 (acetone) |
| 44 | S | $CH_2$ | 2 | H | $CH_3$ | $NH-C(CH_3)_2-C\equiv CH$ | H | H | 226–227 ($Et_2O$-MeOH)[2] |
| 45 | S | $CH_2$ | 2 | 3-$CH_3$ | $CH_3$ | $-NH-(CH_2)_4-C_6H_5$ | H | H | 108–110 (acetone) |
| 46 | S | $CH_2$ | 2 | H | $CH_3$ | $-NH-(CH_2)_2OCH_2-C_6H_5$ | H | H | 96–98 (acetone) |
| 47 | S | $CH_2$ | 1 | H | $CH_3$ | $-NH-(CH_2)_2-O-C_6H_5$ | H | H | 131–132 (acetone) |
| 48 | S | $CH_2$ | 2 | 3-$CH_3$ | $CH_3$ | $-NH-(CH_2)_3-C_6H_5$ | H | H | 100–102 (acetone) |
| 49 | S | $CH_2$ | 2 | 3-$CH_3$ | $CH_3$ | $-NH-(CH_2)_2-O-C_6H_5$ | H | H | 85–87 (acetone) |
| 50 | S | $CH_2$ | 2 | H | $CH_3$ | $-NH(CH_2)_3O(CH_2)_3CH_3$ | H | H | 89.0 (hexane) |
| 51 | S | $CH_2$ | 2 | H | $CH_3$ | $-NHcycloC_3H_5$ | H | H | 96–97 (acetone) |
| 52 | S | $CH_2$ | 2 | H | $CH_3$ | −NHadamantyl | H | H | 114–115 (acetone) |
| 53 | S | $CH_2$ | 2 | H | $CH_3$ | $-NH-(CH_2)_2-O-C_6H_4-OCH_3$ | H | H | 109–110 (acetone) |
| 54 | S | $CH_2$ | 2 | H | $CH_3$ | $-NH-(CH_2)_2-O-C_6H_4-OCH_3$ | H | H | 132–133 (acetone) |
| 55 | O | $CH_2$ | 1 | 2$CH_3$ | $CH_3$ | $-NHnC_8H_{17}$ | H | H | 94.5 (acetonitrile) |

TABLE I-continued

| Cpd. # | X | Y | n | R¹ | R² | $-N\begin{smallmatrix}R^3\\R^4\end{smallmatrix}$ | R⁵ | R⁶ | MP (°C.) [1][4] |
|---|---|---|---|---|---|---|---|---|---|
| 56 | S | CH₂ | 2 | H | CH₃ | 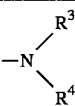 | H | H | 101–102 (acetone) |
| 57 | S | CH₂ | 1 | H | CH₃ | 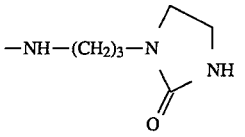 | H | H | 128–129 (acetone) |
| 58 | S | CH₂ | 1 | 2CH₃ | CH₃ | 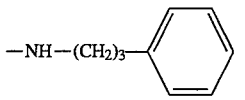 | H | H | 108–109 (acetone) |
| 59 | S | CH₂ | 2 | H | CH₃ | 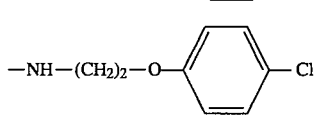 | H | H | 258.5 (MeOH-Et₂O)[3] |
| 60 | S | CH₂ | 1 | H | CH₃ | 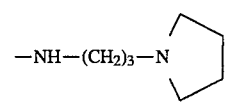 | H | H | 109–110 (acetone) |
| 61 | S | CH₂ | 1 | 2CH₃ | CH₃ | 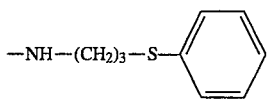 | H | H | 109–111 (MeOH) |
| 62 | O | CH₂ | 1 | 2CH₃ | CH₃ | 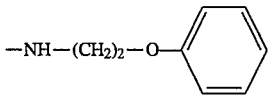 | H | H | 250.8 (EtOH)[3] |
| 63 | S | CH₂ | 1 | H | CH₃ | 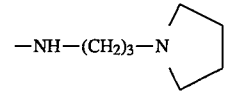 | H | H | 175–178 (MeOH-Et₂O)[2] |
| 64 | S | CH₂ | 1 | 2CH₃ | CH₃ | 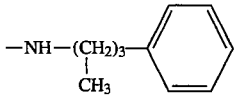 | H | H | 177–179 (MeOH-Et₂O)[2] |
| 65 | O | CH₂ | 1 | 2CH₃ | CH₃ | 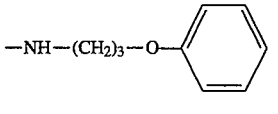 | H | H | 107.8 (cyclohexane) |
| 66 | S | CH₂ | 1 | 2CH₃ | CH₃ | 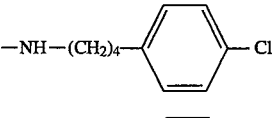 | H | H | 121–122 (acetone) |
| 67 | S | CH₂ | 1 | 2CH₃ | CH₃ | 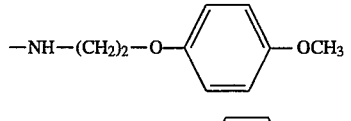 | H | H | 85–87 (Et₂O) |
| 68 | S | CH₂ | 1 | 2CH₃ | CH₃ | 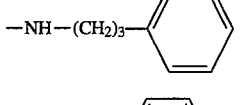 | H | H | 88–90 (Et₂O) |

TABLE I-continued

| Cpd. # | X | Y | n | R¹ | R² | −N(R³)(R⁴) | R⁵ | R⁶ | MP (°C.) (1)(4) |
|---|---|---|---|---|---|---|---|---|---|
| 69 | O | CH₂ | 1 | 2CH₃ | CH₃ | −NH−(CH₂)₃−C₆H₅ | H | H | 96.9 (isoPrOH-hexane) |
| 70 | O | CH₂ | 1 | 2CH₃ | CH₃ | −NH−(CH₂)₄−C₆H₅ | H | H | 110.7 (cyclohexane) |
| 71 | S | CH₂ | 1 | 2CH₃ | CH₃ | −NH−(CH₂)₄−C₆H₄−CH₃ | H | H | 86–88 (acetone) |
| 72 | S | CH₂ | 2 | H | CH₃ | −NH−(CH₂)₃O(CH₂)₂OnC₄H₉ | H | H | 82.0 (pentane-cyclohexane) |
| 73 | S | CH₂ | 2 | H | CH₃ | −NH−(CH₂)₁₀COOCH₃ | H | H | 108–109 (MeOH) |
| 74 | O | CH₂ | 1 | 2CH₃ | CH₃ | −NH−(CH₂)₃O−(CH₂)₃CH₃ | H | H1 | 52.3 (C₆H₆-cyclohexane)⁽²⁾ |
| 75 | S | CH₂ | 2 | H | CH₃ | −NH−(CH₂)₃−C₆H₅ | H | H | 113–114 (acetone) |
| 76 | S | CH₂ | 2 | H | CH₃ | −NHnC₁₄H₂₉ | H | H | 110–112 (MeOH) |
| 77 | S | CH₂ | 2 | H | CH₃ | −NH−(CH₂)₃−N(CH₂CH₂NH)C=O | H | H | 102–104 (acetone) |
| 78 | S | CH₂ | 2 | H | CH₃ | −NH−(CH₂)₃−C₆H₄−Cl | H | H | 84–86 (acetone) |
| 79 | S | CH₂ | 1 | 2CH₃ | CH₃ | −NH−(CH₂)₂−O−C₆H₄−CH₃ | H | H | 129–130 (acetone) |
| 80 | S | CH₂ | 2 | H | CH₃ | −NH−(CH₂)₃S(CH₂)₃CH₃ | H | H | 93.6 (hexane) |
| 81 | S | CH₂ | 2 | H | CH₃ | −NH−(CH₂)₃O(CH₂)₂OCH₃ | H | H | 79.0 (cyclohexane) |
| 82 | O | CH₂ | 1 | 2CH₃ | CH₃ | −NHCH(CH₃)−(CH₂)₃−C₆H₅ | H | H | 195 (isoPrOH)⁽²⁾ |
| 83 | S | CH₂ | 2 | H | CH₃ | −NH−(CH₂)₂−O−(indanyl) | H | H | 208.9 (CH₂Cl₂) |
| 84 | O | CH₂ | 1 | 2CH₃ | CH₃ | −NH−(CH₂)₂−O−C₆H₄−Cl | H | H | 74 (toluene-pentane) |

TABLE I-continued

| Cpd. # | X | Y | n | R¹ | R² | $-N\begin{smallmatrix}R^3\\R^4\end{smallmatrix}$ | R⁵ | R⁶ | MP (°C.) [1][4] |
|---|---|---|---|---|---|---|---|---|---|
| 85 | S | CH₂ | 1 | H | CH₃ | —NH—(CH₂)₂—O—C₆H₄—CN | H | H | 86–88 (acetone) |
| 86 | S | CH₂ | 1 | H | CH₃ | —NH—(CH₂)₂—O—C₆H₄—NHCOCH₃ | H | H | 119–121 (MeOH-acetone) |
| 87 | S | CH₂ | 2 | H | CH₃ | —NH—(CH₂)₂—O—C₆H₄—NHCOCH₃ | H | H | 120–121 (MeOH-Et₂O)[2] |
| 88 | S | CH₂ | 2 | H | CH₃ | —NH—(CH₂)₂—O—naphthyl | H | H | 185.4 (H₂O) |
| 89 | O | CH₂ | 1 | 2CH₃ | CH₃ | —NH—(CH₂)₂—O—C₆H₅ | H | H | 99.1 (cyclohexane) |
| 90 | O | CH₂ | 1 | 2CH₃ | CH₃ | —NH—(CH₂)₄—C₆H₄—CH₃ | H | H | 108.9 (cyclohexane) |
| 91 | S | CH₂ | 2 | H | CH₃ | —N(piperidinyl)-phenyl | H | H | 116.1 (cyclohexane) |
| 92 | S | CH₂ | 1 | H | CH₃ | —NH—(CH₂)₉—CH=CH₂ | H | H | 107–109 (methanol) |
| 93 | S | CH₂ | 2 | H | CH₃ | —NHnC₈H₁₇ | 8CH₃ | H | 129–130 (CHCl₃) |
| 94 | S | CH₂ | 2 | H | CH₃ | —NH(CH₂)₄—C₆H₅ | 8CH₃ | H | 131–132 (CHCl₃) |
| 95 | S | CH₂ | 2 | H | CH₃ | —NH(CH₂)₃—O—C₆H₅ | 8CH₃ | H | 136–137 (CHCl₃-Et₂O) |
| 96 | S | CH₂ | 2 | H | CH₃ | —NH(CH₂)₃—S—C₆H₅ | 8CH₃ | H | 121–122 (CHCl₃-Et₂O) |
| 97 | S | CH₂ | 1 | H | CH₃ | —NHnC₈H₁₇ | H | H | 81–83 (acetone)[5] |
| 98 | S | CH₂ | 1 | H | CH₃ | —NH(CH₂)₄—C₆H₅ | H | H | 85–87 (acetone)[5] |
| 99 | S | CH₂ | 1 | H | CH₃ | —NH(CH₂)₄—C₆H₅ | H | COC(CH₃)₃ | 177–179 (isoprOH)[2] |

TABLE I-continued

| Cpd. # | X | Y | n | R¹ | R² | —N(R³)(R⁴) | R⁵ | R⁶ | MP (°C.) [1][4] |
|---|---|---|---|---|---|---|---|---|---|
| 100 | S | S | 2 | H | CH₃ | —NH(CH₂)₄—C₆H₅ | H | H | 138–140 (MeOH) |
| 101 | S | S | 2 | H | CH₃ | —NHnC₈H₁₇ | H | H | 108–109 (acetone) |
| 102 | S | CH₂ | 2 | H | CH₃ | —NH(CH₂)₃—CO—C₆H₄—F | H | H | 181.6 (MeOH/isoprOH)[2] |
| 103 | S | CH₂ | 1 | H | CH₃ | —NH(CH₂)₄—O—C₆H₄—NHSO₂CH₃ | H | H | 160–161 (MeOH) |
| 104 | S | S | 2 | H | CH₃ | —NH(CH₂)₂—O—C₆H₅ | H | H | 130–132 (CHCl₃) |
| 105 | O | CH₂ | 1 | 2CH₃ | CH₃ | —NH(CH₂)₃—CO—C₆H₄—F | H | H | 184.9 (MeOH/isoprOH)[2] |
| 106 | S | CH₂ | 1 | 2CH₃ | CH₃ | —NH(CH₂)₂—S—C₆H₅ | H | H | 100–101 (MeOH) |
| 107 | S | CH₂ | 2 | H | CH₃ | —NH(CH₂)₂—O—C₆H₄—C(CH₃)₃ | H | H | 138.0 (hexane) |
| 108 | S | CH₂ | 1 | H | CH₃ | —NH(CH₂)₂—O—C₆H₄—COC₂H₅ | H | H | 176–177 (MeOH-Et₂O)[2] |
| 109 | S | CH₂ | 1 | 3CH₃ | CH₃ | —NH(CH₂)₄—C₆H₅ | H | H | 102–103 (MeOH) |
| 110 | S | CH₂ | 2 | H | CH₃ | morpholine with CH₃ and C₆H₅ substituents | H | H | 200.3 (MeOH/AcOEt) |
| 111 | S | CH₂ | 1 | H | CH₃ | —NH(CH₂)₃CO—C₆H₄—F | H | H | 178–179 (MeOH)[2] |
| 112 | S | CH₂ | 1 | H | CH₃ | —NH(CH₂)₄—C₆H₅ | H | COCH₃ | 159.1 (acetonitrile)[2] |
| 113 | S | CH₂ | 1 | H | CH₃ | —NH(CH₂)₄—C₆H₅ | H | COCH₃ | 179.1 (MeOH/Et₂O)[5][2] |

TABLE I-continued

| Cpd. # | X | Y | n | R¹ | R² | -N(R³)(R⁴) | R⁵ | R⁶ | MP (°C.) [1][4] |
|---|---|---|---|---|---|---|---|---|---|
| 114 | O | CH₂ | 1 | CH₃ | CH₃ | —NH(CH₂)₂—O—C₆H₄—COOCH₃ | H | H | 113–115 (acetone) |
| 115 | S | CH₂ | 1 | H | C₂H₅ | —NH(CH₂)₄—C₆H₅ | H | H | 72–73 (MeOH) |
| 116 | S | CH₂ | 1 | 2CH₃ | CH₃ | —NH(CH₂)₂—O—C₆H₄—COC₂H₅ | H | H | 191–192 (MeOH-Et₂O)[2] |
| 117 | S | CH₂ | 1 | H | CH₃ | —NH(CH₂)₄—C₆H₅ | H | COC(CH₃)₂ | 167.4 (acetonitrile)[2] |
| 118 | S | CH₂ | 1 | H | CH₃ | —NH(CH₂)₄—C₆H₅ | H | COC₂H₅ | 169.9 (acetonitrile)[2] |
| 119 | S | CH₂ | 1 | H | C₂H₅ | —NHnC₈H₁₇ | H | H | 78–80 (MeOH) |
| 120 | S | CH₂ | 1 | 2CH₃ | CH₃ | —NH(CH₂)₂OCH₂—C₆H₅ | H | H | 144–145 (MeOH-Et₂O)[2] |
| 121 | O | S | 2 | H | CH₃ | —NHnC₈H₁₇ | H | H | 170–172 (MeOH)[2] |
| 122 | O | S | 2 | H | CH₃ | —NH(CH₂)₄—C₆H₅ | H | H | 95–97 (MeOH) |
| 123 | O | S | 2 | H | CH₃ | —NH(CH₂)₂—O—C₆H₅ | H | H | 116–118 (MeOH) |
| 124 | O | S | 2 | H | CH₃ | —NH(CH₂)₃SnC₄H₉ | H | H | 64–65 (Et₂O-hexane) |
| 125 | S | CH₂ | 1 | H | CH₃ | —NH(CH₂)₃SnC₄H₉ | H | H | 196.2 (acetonitrile)[2] EtOH) |
| 126 | S | CH₂ | 1 | H | C₂H₅ | —NH(CH₂)₂—O—C₆H₅ | H | H | 86–88 (acetone) |
| 127 | S | CH₂ | 2 | H | CH₃ | —NHnC₈H₁₇ | H | H | 52–53 (hexane)[5] |
| 128 | S | CH₂ | 2 | H | C₂H₅ | —NHnC₈H₁₇ | H | H | 167–168 (Et₂O-MeOH)[2] |
| 129 | S | CH₂ | 1 | H | CH₃ | —NH(CH₂)₃O(CH₂)₂OCH₃ | H | H | 152.2 (acetonitrile)[2] |
| 130 | S | CH₂ | 1 | H | CH₃ | —NH(CH₂)₄—C₆H₅ | H | COnC₃H₇ | 151.4 (acetonitrile)[2] |
| 131 | S | CH₂ | 2 | H | CH₃ | —NHnC₈H₁₇ | H | COC₂H₅ | 139.4 (AcOEt)[2] |

TABLE I-continued

| Cpd. # | X | Y | n | R¹ | R² | -N(R³)(R⁴) | R⁵ | R⁶ | MP (°C.) [1][4] |
|---|---|---|---|---|---|---|---|---|---|
| 132 | S | CH$_2$ | 1 | H | CH$_3$ | —NH(CH$_2$)$_4$—C$_6$H$_5$ | H | COcyclo-C$_4$H$_7$ | 131.7 (AcOEt)[2] |
| 133 | S | CH$_2$ | 1 | H | CH$_3$ | —NH(CH$_2$)$_4$—C$_6$H$_5$ | H | COnC$_7$H$_{15}$ | 145.2 (acetonitrile/isoPrOH)[2] |
| 134 | S | CH$_2$ | 2 | H | CH$_3$ | —NHnC$_8$H$_{17}$ | H | COnC$_3$H$_7$ | 156.2 (AcOEt)[2] |
| 135 | S | CH$_2$ | 2 | H | C$_2$H$_5$ | —NH(CH$_2$)$_4$—C$_6$H$_5$ | H | H | 72–73 (MeOH) |
| 136 | S | CH$_2$ | 2 | H | CH$_3$ | —NHnC$_8$H$_{17}$ | H | COnC$_7$H$_{15}$ | 151.5 (AcOEt)[2] |
| 137 | S | CH$_2$ | 1 | H | CH$_3$ | —NH(CH$_2$)$_4$—C$_6$H$_5$ | H | COcyclo-C$_5$H$_9$ | 158–160 (AcOEt)[2] |
| 138 | S | CH$_2$ | 1 | H | CH$_3$ | —NH(CH$_2$)$_4$—C$_6$H$_5$ | H | COcyclo-C$_6$H$_{11}$ | 148–150 (acetonitrile)[2] |
| 139 | S | CH$_2$ | 2 | H | CH$_3$ | —NHnC$_8$H$_{17}$ | H | COCH(CH$_3$)$_2$ | 126.6 (AcOEt)[2] |
| 140 | S | CH$_2$ | 2 | H | CH$_3$ | —NHnC$_8$H$_{17}$ | H | COCH$_3$ | 148.5 (AcOEt)[2] |
| 141 | S | CH$_2$ | 2 | H | CH$_3$ | —NH(CH$_2$)$_8$CH═CH—nC$_8$H$_{17}$ | H | H | 97–98 (acetone) |
| 142 | S | CH$_2$ | 2 | H | CH$_3$ | —NHnC$_8$H$_{17}$ | H | COcyclo-C$_5$H$_9$ | 156.5 (AcOEt)[2] |
| 143 | S | CH$_2$ | 2 | H | CH$_3$ | —NHCH$_2$CH═C(CH$_3$)—(CH$_2$)$_2$—CH═C(CH$_3$)$_2$ | H | H | 75–77 (Et$_2$O) |
| 144 | S | CH$_2$ | 2 | H | CH$_3$ | —NHnC$_8$H$_{17}$ | H | COC(CH$_3$)$_3$ | 149.4 (AcOEt)[2] |
| 145 | S | CH$_2$ | 2 | H | CH$_3$ | —NHnC$_8$H$_{17}$ | H | COcyclo-C$_4$H$_7$ | 144.6 (AcOEt)[2] |
| 146 | S | CH$_2$ | 2 | H | CH$_3$ | —NHnC$_8$H$_{17}$ | H | COcyclo-C$_6$H$_{11}$ | 182.9 (AcOEt)[2] |
| 147 | S | CH$_2$ | 2 | H | CH$_3$ | —NHnC$_{18}$H$_{17}$ | H | H | 122–123 (CHcl$_3$) |
| 148 | S | CH$_2$ | 1 | H | CH$_3$ | —NH(CH$_2$)$_2$O—C$_6$H$_3$Cl$_2$ (3,4-diCl) | H | H | 118.1 (isoPrOH-hexane) |
| 149 | S | CH$_2$ | 2 | H | CH$_3$ | —NHnC$_{12}$H$_{25}$ | H | H | 93–101 (MeOH—CHCl$_3$) |
| 150 | S | CH$_2$ | 3 | H | CH$_3$ | —NH(CH$_2$)$_4$—C$_6$H$_5$ | H | COC$_2$H$_5$ | 150–152 (MeOH-Et$_2$O)[2] |
| 151 | S | CH$_2$ | 1 | H | CH$_3$ | —NH—(CH$_2$)$_3$O—C(CH$_3$)$_2$—C≡CH | H | H | 107.1 (hexane) |
| 152 | S | CH$_2$ | 2 | H | CH$_3$ | —NH—(CH$_2$)$_6$—C≡CH | H | H | 105–107 (MeOH) |

TABLE I-continued

| Cpd. # | X | Y | n | R¹ | R² | -N(R³)(R⁴) | R⁵ | R⁶ | MP (°C.) [1][4] |
|---|---|---|---|---|---|---|---|---|---|
| 153 | S | CH₂ | 2 | H | CH₃ | —NH—(CH₂)₄—C₆H₅ | H | H | 128–130 (MeOH-Et₂O)[2][5] |
| 154 | NH | CH₂ | 1 | H | CH₃ | —NHnC₈H₁₇ | H | H | 84–85 (acetone-H₂O) |
| 155 | S | CH₂ | 1 | H | CH₃ | —NH—(CH₂)₆—C≡CH | H | H | 113–115 (MeOH) |
| 156 | S | CH₂ | 2 | H | CH₃ | —NH(CH₂—CH=C(CH₃)—CH₂)₂—CH₂—CH=C(CH₃)₂ | H | H | 52–55 (Et₂O) |
| 157 | S | CH₂ | 2 | 2(CH₃)₂ | CH₃ | —NH—(CH₂)₄—C₆H₅ | H | H | 121.8 (CH₃CN) |
| 158 | S | CH₂ | 2 | 2(CH₃)₂ | CH₃ | —NH—(CH₂)₂—O—C₆H₅ | H | H | 125.5 (CH₃CN) |
| 159 | NH | CH₂ | 1 | H | CH₃ | —NH—(CH₂)₂—O—C₆H₅ | H | H | 90–91 (CH₃CN—H₂O) |
| 160 | NH | CH₂ | 1 | H | CH₃ | —NH—(CH₂)₄—C₆H₅ | H | H | 78–80 (CH₃CN) |
| 161 | S | CH₂ | 2 | 2 COOH | CH₃ | —NHnC₈H₁₇ | H | H | 125–127 (MeOH-Et₂O) |
| 162 | S | CH₂ | 2 | H | CH₃ | —NH—(CH₂)₆—C≡C—nC₄H₉ | H | H | 86–88 (MeOH) |
| 163 | CH₂ | CH₂ | 1 | H | CH₃ | —NH—(CH₂)₄—C₆H₅ | H | H | 108–110 (acetone) |
| 164 | CH₂ | CH₂ | 1 | H | CH₃ | —NHnC₈H₁₇ | H | H | 98–100 (acetone) |
| 165 | CH₂ | CH₂ | 1 | H | CH₃ | —NH—(CH₂)₃—C₆H₅ | H | H | 111.9 (acetonitrile) |
| 166 | CH₂ | CH₂ | 1 | H | CH₃ | —NH—(CH₂)₄—C₆H₄—CH₃ | H | H | 126.6 (hexane) |
| 167 | CH₂ | CH₂ | 1 | H | CH₃ | —NH—(CH₂)₄—C₆H₄—Cl | H | H | 109–110 (acetone) |
| 168 | CH₂ | CH₂ | 1 | H | CH₃ | —NH—(CH₂)₂—O—C₆H₅ | H | H | 122.2 (hexane) |
| 169 | CH₂ | CH₂ | 1 | H | CH₃ | —NH—(CH₂)₂—O—C₆H₄—Cl | H | H | 132.4 (acetone) |

TABLE I-continued

| Cpd. # | X | Y | n | R¹ | R² | -N(R³)(R⁴) | R⁵ | R⁶ | MP (°C.) [1][4] |
|---|---|---|---|---|---|---|---|---|---|
| 170 | $CH_2$ | $CH_2$ | 2 | H | $CH_3$ | —NHnC₈H₁₇ | H | H | 97.2 (acetone) |
| 171 | $CH_2$ | $CH_2$ | 2 | H | $CH_3$ | —NH—(CH₂)₄—C₆H₅ | H | H | 99.7 |
| 172 | $CH_2$ | $CH_2$ | 1 | H | $CH_3$ | N-piperidinyl-4-CH₂—C₆H₅ | H | H | 112.9 (acetone) |
| 173 | $CH_2$ | $CH_2$ | 1 | H | $CH_3$ | —NH—CH(CH₃)—(CH₂)₃—C₆H₅ | H | H | 213 (isoPrOH)[2] |
| 174 | $CH_2$ | $CH_2$ | 1 | H | $CH_3$ | N-piperidinyl-4-C₆H₅ | H | H | 210.8 (isoPrOH)[2] |
| 175 | $CH_2$ | $CH_2$ | 1 | H | $CH_3$ | —NH—(CH₂)₃—CO—C₆H₄—F | H | H | 180.7 (MeOH/isoPrOH)[2] |
| 176 | $CH_2$ | $CH_2$ | 1 | H | $CH_3$ | —NH—(CH₂)₂—O—C₆H₄—C(CH₃)₃ | H | H | 102.2 (hexane) |
| 177 | $CH_2$ | $CH_2$ | 1 | H | $CH_3$ | N-morpholinyl(CH₃)(C₆H₅) | H | H | 177.1 (MeOH/AcOEt)[2] |
| 178 | $CH_2$ | $CH_2$ | 1 | H | $CH_3$ | —NH—(CH₂)₃SnC₄H₉ | H | H | 82.1 (acetone) |
| 179 | $CH_2$ | $CH_2$ | 1 | H | $CH_3$ | —NH(CH₂)₃O(CH₂)OCH₃ | H | H | 134.9 (benzene-cyclohexane)[2] |
| 180 | $CH_2$ | $CH_2$ | 1 | H | $CH_3$ | —NH(CH₂)₂—O—C₆H₅ | H | $COCH_3$ | 129–131 (acetonitrile)[2] |
| 181 | $CH_2$ | $CH_2$ | 1 | H | $CH_3$ | —NH(CH₂)₄—C₆H₅ | H | $CO(CH_2)_6CH_3$ | oil |
| 182 | $CH_2$ | $CH_2$ | 1 | H | $CH_3$ | —NH(CH₂)₂—O—C₆H₅ | H | $COCH_3$ | 140–141 (acetonitrile)[2][5] |
| 183 | S | $CH_2$ | 1 | H | $CH_3$ | —NH(CH₂)₄—C₆H₅ | H | H | 85–87 (acetonitrile)[5] |
| 184 | S | $CH_2$ | 1 | H | $CH_3$ | —NH(CH₂)₄—C₆H₅ | H | H | [7] |

TABLE I-continued

| Cpd. # | X | Y | n | R¹ | R² | —N(R³)(R⁴) | R⁵ | R⁶ | MP (°C.) [1][4] |
|---|---|---|---|---|---|---|---|---|---|
| 185 | S | $CH_2$ | 1 | H | $CH_3$ | —NH(CH₂)₄—C₆H₅ | H | H | [8] |
| 186 | S | $CH_2$ | 1 | H | $CH_3$ | —N(piperidinyl)—CH₂—C₆H₅ | H | H | |

(1) The recrystallization solvent is given between brackets; the melting point mentioned is that of the free base, unless otherwise stated.
(2) Melting point of the hydrochloride.
(3) Melting point of the dihydrochloride.
(4) The elemental analyses were made for elements C, H, N and were found to conform to the theoretical values.
(5) Threo form.
(6) Erythro form.
(7) Optical isomer: (−)-tibalosine.
(8) Optical isomer: (+)-tibalosine.

The term "hydrido" denotes a single hydrogen atom (H). This hydrido group may be attached, for example, to an oxygen atom to form a hydroxyl group; or, as another example, one hydrido group may be attached to a carbon atom to form a >CH— group; or, as another example, two hydrido groups may be attached to a carbon atom to form a —CH₂— group. Where the term "alkyl" is used, either alone or within other terms such as "haloalkyl" and "hydroxyalkyl", the term "alkyl" embraces linear or branched radicals having one to about twenty carbon atoms or, preferably, one to about fifteen carbon atoms. More preferred alkyl radicals are "lower alkyl" radicals having one to about twelve carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "polycycloalkyl" denotes a radical having two or more cycloalkyl rings; for example, an alkylene group of one or more methylene radicals may bridge a cycloalkyl ring in one or more places to form an adamantyl group. Preferred polycycloalkyl groups contain 10 to about 20 carbon atoms. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkenylalkyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynylalkyl" embraces linear or branched radicals having two to about twenty carbon atoms, preferably two to about ten carbon-atoms, and containing at least one carbon-carbon triple bond. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methylthio group. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "phenoxy" and "phenthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and $SO_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more preferred sub-class of acyl. The term "heterocyclic" denotes a saturated or partially unsaturated five- or six-membered ring system containing one or more atoms selected from oxygen, sulfur and nitrogen, such as morpholino, piperidinyl, piperizinyl and pyrrolidinyl. The term "heteroaryl" embraces aromatic ring systems containing one or two hetero atoms selected from oxygen, nitrogen and sulfur in a ring system having five or six ring members, examples of which are imidazole, imidazolidione, naphthyl, naphthyloxy, indanoyl, indanoyloxy, thienyl, furanyl, pyridinyl, thiazolyl, pyrimidyl and isoxazolyl. Such heteroaryl may be attached as a substituent through a carbon atom of the heteroaryl ring system, or may be attached through a carbon atom of an oxygen atom or a sulfur atom substituted on a heteroaryl ring-member carbon atom through which the heteroaryl group is attached to the $R^3/R^4$-substituted nitrogen atom of Formula I. Also, such heteroaryl may be attached through a ring nitrogen atom as long as aromaticity of the heteroaryl moiety is preserved after attachment. Such "heterocyclic" and "heteroaryl" groups may be formed so as to include the nitrogen atom of Formula I to which the $R^3$ and $R^4$ substituents are attached.

Also included in the family of compounds of Formula I are isomeric forms including, optical isomers, enantiomers and diastereoisomers. Also included in this invention are the pharmaceutically-acceptable salts of the Formula I compounds. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethane sulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of general Formula I can possess one or more asymmetic carbon atoms and are thus capable to existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocycanate.

The synthesized diastereoisomers can be separated by conventional means such as chromatography, distillation, crystallization or sublimation, and then hydrolyzed to deliver the enantiomericaly pure compound. The optically active compounds of Formula I can likewise be obtained by utilizing optically active starting materials. These isomers may be in the form of a free acid, a free base, an ester or a salt.

Biological Evaluation

The NMDA receptor-ionophore complex consists of a number of interacting domains, including one for polyamines where ifenprodil binds to exert its noncompetitive antagonism. Ifenprodil was iodinated with $Na^{125}I$/chloramine-T, purified and its binding characterized. In cortical membranes, binding of $[^{125}I]$ifenprodin was saturable ($K_d$145 nM, $B_{max}$ 2.5 pmol/mg protein) and to a single site. Specific binding was reversible, being dissociable with 1 mM spermine and poorly dissociable with 1 mM spermine and poorly dissociable with 16.7 µM SL 82.0715, and represented 70–75% of total binding by filtration. In autoradiographic studies using slidemounted sections, binding sites for $[^{125}I]$ifenprodil were localized in several regions including anterior cingulate cortex, hippocampus and amygdala.

Membrane Preparation

Membranes were prepared from freshly dissected brains of adult male Sprague-Dawley rats (175–250 g).

$^{125}I]$Ifenprodil: Crude membranes were prepared from freshly dissected cerebral cortices as described elsewhere [P. M. Beart et al, Neurosci. Lett., 124, 187–189 (1991)]. Briefly, assays were performed in 5 mM Tris HCl pH 7.7 containing $[^{125}I]$ifenprodil (20,000 dpms, ~20 pM) and cortical membranes (0.5 mg wet wt.) in a final volume of 0 5 mL Incubations were for 30 min at 20° C., in triplicate, employing 12 concentrations of competing drugs. Nonspecific binding was defined with 10 mM spermine. Assays were terminated by rapid filtration through GF/B filter paper and washing [Beart et al, Id., (1991)].

Polyamine-stimulated $[^3H]$TCP: Crude synaptic ("buffy coat") membranes were prepared from freshly dissected cerebral cortices. Membrane preparations were extensively washed employing 3 freeze-thaw cycles. The final pellet was stored at −70° C. for 1–7 days prior to assay. On the day of assay, the membrane pellet was washed twice by resuspension and centrifugation (45,000 g, 10 min. ). The final membrane pellet was resuspended in 80 volumes of 5 mM Tris HCl pH 7.7 and binding assays were performed in 5 mM Tris HCl pH 7.7, containing $[^3H]$TCP (6 nM) and cortical washed/frozen-thawed synaptic membranes (1.25 mg wet wt., 100 µg protein) in a final volume of 250 µl. Incubations were for 60 min. at 25° C. employing 6 concentrations of spermidine (6.67–100 µM) in triplicate determinations in the absence and presence of various drugs in the same individual experiment. Assay tubes with no additions (basal) and containing 5 µM MK-801 in the absence and presence of drugs were routinely included in each experiment. Assays were terminated by rapid vacuum filtration through GF/B filter paper (pre-soaked in 0.5% aqueous polyethyleneimine) in a Brandel M-48R Cell Harvester and thorough washing with ice-cold 5 mM Tris HCl pH 7.7.

$R(+-^3H]3$-PPP: Crude membranes were prepared from whole brain (minus cerebellum) as described previously [P. M. Beart et al, J. Neurochem., 53, 779–788 (1989)]. A filtration binding assay was employed under similar conditions to those of Largent et al (1986) with 3 nM R $(+)-[^3H]$-3-PPP and a 90 min. incubation at 25° C. (Beart et al, 1989).

Non-specific binding was defined with 10 μ 1,3-di(2-tolyl)guanidine (DTG).

Receptor Autoradiography

Coronal sections of rat brain (10 μm) were thaw-mounted on to gelatin coated, glass microscope slides and stored at −20° C. (overnight–3 days). Procedures for labelling and autoradiography with L[$^3$H]-glutamate (NMDA-sensitive and [$^{125}$I]ifenprodil have been given elsewhere [M. Cincotta et al, *Anal. Biochem.*, 177, 150–155 (1989)]; Beart et al, 1991). Non-specific binding was defined with DL-1-amino-3-hydroxy-5-methyl-4-isoxazolepropionic acid (AMPA) hydrobromide (33 μM) plus kainate (10 μM) and 10 mM spermine, respectively. For [$^3$H] glycine the method was similar to that of Bristow et al (1986) and performed in 50 mM Tris citrate pH 7.4 with 250 nM [$^3$H] ligand and a 20 min. incubation at 20° C. Non-specific binding was defined with 200 μM glycine. For labelling with L[$^3$H]-glutamate and [$^3$H]glycine, sections were preincubated in appropriate buffer, dried in cool air and incubated under 250 μl of incubation buffer.

Data Analysis

Binding data were analyzed by the iterative curve fitting programs EBDA and LIGAND as fully described elsewhere [Beart et al, Id., (1989)]. Results obtained from experiments examining spermidine-stimulated binding of [$^3$H]TCP were analyzed by the program FLEXIFIT [V. Guardabasso et al, *FASEB J.*, 2, 209–215 (1988)] which iteratively fits data to a sigmoidal model providing estimates of $IC_{50}$ and slope for the drug under study.

Reagents

Radioisotopes were obtained from New England Nuclear (Boston, Me.): L[$^3$H]-Glutamate (specific activity 55 Ci/mmole), [$^3$H]Glycine (specific activity 35 Ci/mmole), R(+)-[$^3$H]3-PPP (specific activity 108 Ci/mmole), [$^3$H]TCP (specific activity 60 ci/mmole). Na$^{125}$I (specific activity 2200 Ci/mmole) was purchased from Amersham (Little Chalfront, U.K.). Chemicals were obtained from the following sources: Chloramine-T, Merck (Darmstadt, Germany); glycine, NMDA and kainate, Sigma Chemical Co. (St. Louis, Mo.); AMPA, Dr. P. Krogsgaard-Larsen (Copenhagen, Denmark); caramiphen, dextromethorphan and dextrorphan, Dr. J. Church (Vancouver, Canada); DTG, Dr. E. Weber (Portland, Oreg.); dizocilipine (MK-801), Merck, Sharpe and Dohme (Harlow, U.K.); ifenprodil and SL 82.0715, Synthelabo (Bagneux, France); (+)SKF 10,047 (N-allylnormetazocine), National Institute on Drug Abuse (Rockville, Mass.); Compounds of Table I, G. D. Searle & Co. (Mont-St-Guibert, Belgium); R(+)-3-PPP, Astra (Sodertalje, Sweden). All other reagents were purchased from commercial suppliers.

Binding of [$^{125}$I]Ifenprodil

The binding assay using [$^{125}$I]ifenprodil and filtration methodology gave an excellent signal-to-noise ratio beyond one half-life; under the conditions employed specific binding represented 70–80% of specific binding. [$^{125}$I]Ifenprodil bound rapidly and saturably to a single population of sites: dissociation constant 121 (45–236) nM and density of binding sites 228 (84–619) pmol/mg protein (estimates and 95% confidence intervals, n=3 (Beart et al, 1991). Polyamines completely inhibited specific binding: dissociation constants for spermine and spermidine were 24+13 (n=4) and 44+10 BM (n=3), respectively. The ifenprodil analogue, SL82.0715, exhibited a dissociation constant of 2.3±0.13 μM (n=3).

Autoradiographic Studies With $^{125}$I]Ifenprodil

From a wide range of preliminary experiments, the inclusion of BSA (0.2%) was found to be essential for the demonstration of discretely distributed binding sites for [$^{123}$I]ifenprodil relative to non-specific images. Attempts to employ polyethyleneimine (0.05%) to reduce non-specific binding actually resulted in enhanced binding of [$^{125}$I] ifenprodil to white matter. Autoradiographic labelling patterns revealed heterogeneous labelling of many telencephalic, diencephalic and mesencephalic brain areas see Beart et al, Id, (1991)]. In hippocampus, the topographic labelling pattern was consistent with that generally considered to be NMDA-like ([W. F. Maragos et al, *J. Neuroci.*, 8, 493–501 (1988)]. Labelling observed with $^{125}$I]ifenprodil in cerebellum was over the molecular layer, however, relative to that found for the binding of NMDA-selective [$^3$H]glutamate and [$^3$H]glycine in the granular layer.

Compounds of Table I were evaluated against the binding of [$^{125}$I]ifenprodil and found to also fully inhibit specific binding of [$^{125}$I]ifenprodil (Table II).

Compounds of Table I were also evaluated against spermidine-stimulated bind of [$^3$H]TCP, since this system represents a convenient functional model of the coupling of the polyamine domain to the NMDA ionophore [R. W. Ransom et al, *J. Neurochem.*, 51, 830–836 (1988)]. All tested compounds of Table I were found to inhibit polyamine-stimulated binding of [$^3$H]TCP in an apparently non-competitive manner, i.e., the inhibition was concentration dependent, but maximal stimulation of binding by spermidine was reduced (Table II). Computerized-analyses of inhibition data suggested that the mechanism of inhibition by Compounds of Table I was competitive with respect to spermidine.

TABLE II

POLYAMINE DOMAIN INTERACTION

| COMPOUND # | [$^{125}$I] IFENPRODIL $K_d$ (μM) | SPERMIDINE [$^3$H] TCP $IC_{50}$ (μM) |
|---|---|---|
| 7 | 3.6 ± 0.3 | 8.2 |
| 183 | 9.3 ± 5.4 | + |
| 184 | 6.3 ± 1.8 | + |
| 185 | 3.5 ± 1.1 | 59 |
| 2 | 9.3 ± 5.5 | + |
| 186 | 6.7 ± 1.1 | + |
| 26 | 12 | N.T. |
| 42 | 2.7 ± 0.4 | + |
| 75 | 5.0 ± 1.4 | + |
| 24 | 3.7 ± 1.1 | + |
| Ifenprodil | 0.15 ± 0.03 | 6.8 |
| Nylidrin | 30 ± 8.5 | 73 |
| SL82.0715 | 2.3 ± 0.1 | N.T. |

Values are mean ± s.e.m. (n = 3 or 4 observations). At least two independent experiments were performed in studies of polyamine-stimulated binding of [$^3$H]TCP. N.T. = not tested.
+ = inhibitory at 50 μM.

Compounds of Table I inhibited the binding of R(+)-[$^3$H] 3-PPP. This type of binding has been previously demonstrated to label a binding site with the characteristics of a sigma site [Beart et al, Id., (1989)]. Compound #185 and Compound #186 were found to be very potent inhibitors of the binding of R(+)-[$^3$H]3-PPP (Table III). For all of the tested Compounds of Table I the pattern of inhibition of binding yielded Hill coefficients <1. Further analyses suggested that the interaction of Compounds of Table I, ifenprodil and nylidrin with the site labelled by R(+)-[$^3$H]3-PPP, was better described by a two-site model (Table III). The proportion of sites in the high affinity state was generally in the range of 60–80% of the total sites. These computer-assisted analyses revealed that Compound #7 possessed appreciable affinity for the high affinity sigma site, as did its two enantiomers, Compound #184 and Compound #185.

TABLE III

| | Sigma Site Binding | | | |
|---|---|---|---|---|
| COMPOUND # | $K_G$ (nM) | $K_H$ (nM) | $K_L$ (μM) | % $R_H$ |
| 7 | 170 | 44 | 11 | 66 |
| 183 | 450 | (300) | (130) | (84) |
| 184 | 230 | 6.1 | 6.1 | 54 |
| 185 | 32 | (4.6) | (0.3) | (63) |
| 2 | 400* | (150) | (4.3) | (72) |
| 186 | 30 | (2.9) | (0.6) | (72) |
| 75 | 340 | 86 | 4.3 | 67 |
| 24 | 390* | (89) | (3.0) | (63) |
| Ifenprodil | 20 | 11 | 19 | 82 |
| Nylidrin | 38 | 19 | 11 | 86 |
| (+)SKF10.047 | 1500 | 48 | 6.3 | 60 |

Values are from analyses of pooled data files; n = 2 independent experiments.
*one experiment. Binding data fitted better to 2 site model (P < 0.05), except when values in parentheses (P < 0.05).
$K_G$ = Dissociation constant for one site fit
$K_H$ = Dissociation constant at high affinity site for two site fit
$K_L$ = Dissociation constant at low affinity site for two site fit
% $R_H$ = Percent of high affinity binding sites for two site fit Compounds of Formula I would be useful to treat various CNS-related diseases. Biological evaluation of representative compounds of Formula I shows that such compounds are potent inhibitors mediators interacting at the NMDA receptor site complex. From data shown in Table II, it is evident that compounds of Formula I would be useful as neuroprotective agents. For example, such compounds would be useful to reduce or control neurotoxic injury associated with conditions of hypoxia, anoxia, or ischemia. These conditions may result from stroke, cardiac arrest such as resulting from myocardial infarct, perinatal asphyxia, head trauma, hypoglycemia, epilepsy, septicemia and similar events. Also, as is evident from the data in Table II, compounds of Formula I would be useful to treat various neuroegenerative disease states linked to excitotoxic actions at the NMDA receptor complex. Examples of such disease states are Parkinson's disease, Huntington's chorea and Alzheimer's disease. As shown by sigma binding data of Table III, compounds of Formula I would be useful to treat various psychotic disorders such as schizophrenia. As used herein, the phrase "therapeutically-effective amount" is that amount of compound of Formula I administered to a subject which would be useful to alleviate or moderate a CNS-related disease in a subject afflicted with, or susceptible to, such disease.

Administration of compounds within Formula I to humans can-be. by any technique capable of introducing the compounds into the bloodstream of a human patient, including oral administration, and by intravenous, intramuscular and subcutaneous injections.

Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation, although in some acute-care situations a compound of Formula I may be administered alone. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain controlledrelease formulation as may be provided in a dispersion of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method to treat the neuropathological consequences of neurotoxic injury or neurodegenerative disease mediated by an NMDA receptor in a subject, which method comprises administering to said subject a therapeutically-effective amount of a compound of Formula I:

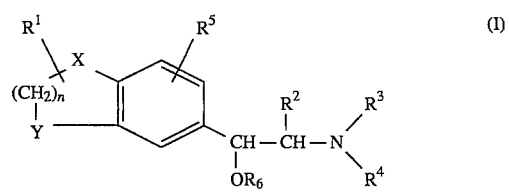

wherein X is selected from oxygen atom, sulfur atom, —$CH_2$— and —NH—;

wherein Y is selected from —$CH_2$— and —NH—;

wherein n is a number selected from one through three, inclusive;

wherein $R^1$ is selected from hydrido, alkyl, hydroxyalkyl, alkoxyalkyl, cycloalkyl, cycloalkylalkyl, phenyl and carboxyl;

wherein $R^2$ is selected from hydrido, alkyl, hydroxyalkyl, cycloalkyl and cyctoalkylalkyl;

wherein each of $R^3$ and $R^4$ is independently selected from hydrido, alkyl, haloalkyl, cycloalkyl, cycloalkylalkyl, alkylcycloalkyl, alkylcycloalkylalkyl, phenyl, phenylalkyl, diphenylalkyl, alkylphenyl, alkylphenylalkyl, halophenyl, halophenylalkyl, phenoxyalkyl, halophenoxyalkyl, alkoxyphenoxyalkyl, cyanophenoxyalkyl, benzyloxyalkyl, alkoxyalkyl, alkoxyalkoxyalkyl, alkoxycarbonylalkyl, phenylthioalkyl, alkylcarbonylaminophenylalkyl, halophenylcarbonylalkyl, halobenzylcarbonylalkyl, alkylcarbonylphenoxyalkyl, alkoxycarbonylphenoxyalkyl, alkylphenoxyalkyl, alkenylalkyl, alkynylalkyl, alkynylalkyloxyalkyl, polycycloalkyl, saturated or partially unsaturated heterocyclic, saturated or partially unsaturated heterocyclicalkyl, heteroarylalkyl and heteroaryloxyalkyl;

wherein $R^3$ and $R^4$ may be taken together to form a saturated or partially unsaturated heterocyclic group or a heteroaryl group, either of which groups may be further substituted, said groups selected from alkylphenylpiperidinyl, morpholino, phenylmorpholino, alkylmorpholino, 1-alkyl-2-phenylmorpholino, phenylalkylpiperidinyl, phenylpiperidinyl, phenylalkylpyrrolidinyl and phenylalkylpiperazinyl;

wherein $R^5$ is selected from hydrido, alkyl, hydroxyalkyl, cycloalkyl, cycloalkylalkyl, phenylalkyl and phenyl;

wherein $R^6$ is selected from hydrido, alkanoyl and cycloalkanoyl;

and wherein any of the foregoing $R^1$–$R^6$ radicals may be further substituted at a substitutable position with a radical selected from alkyl, cycloalkyl, cycloalkylalkyl, alkoxy, alkenylalkyl, alkoxyalkyl, hydroxyalkyl, oxo, cyano, halo, phenyl and phenylalkyl;

or a pharmaceutically-acceptable salt thereof.

2. The method of claim 1 wherein said neurotoxic injury is associated with stroke.

3. The method of claim 1 wherein said neurotoxic injury is associated with myocardial infarction.

4. The method of claim 1 wherein said neurotoxic injury is associated with perinatal asphyxia.

5. The method of claim 1 wherein said neurotoxic injury is associated with head trauma.

6. The method of claim 1 wherein said neurotoxic injury is associated with hypoglycemia.

7. The method of claim 1 wherein said neurotoxic injury is associated with epilepsy.

8. The method of claim 1 wherein said neurotoxic injury is associated with septicemia.

9. The method of claim 1 wherein said neuropathological consequences are from a neurodegenerative disease.

* * * * *